United States Patent
Schneiter

(10) Patent No.: US 6,533,763 B1
(45) Date of Patent: Mar. 18, 2003

(54) HARMONIC FLOW CATHETER

(76) Inventor: James A. Schneiter, 200 Dover Cir., Lake Forest, IL (US) 60045

( * ) Notice: Subject to any disclaimer, the term of this patent is extended or adjusted under 35 U.S.C. 154(b) by 0 days.

(21) Appl. No.: 09/455,078

(22) Filed: Dec. 6, 1999

(51) Int. Cl.$^7$ ............................................... A61M 25/00
(52) U.S. Cl. ...................................... 604/264; 604/523
(58) Field of Search ................................. 604/264, 253, 604/523, 524, 525, 526, 527, 528, 529, 530–539, 43, 265, 266, 267, 271, 274

(56) References Cited

U.S. PATENT DOCUMENTS

| | | | |
|---|---|---|---|
| 4,327,722 A | 5/1982 | Groshong et al. | |
| 4,392,855 A | * 7/1983 | Oreopoulos et al. | ........ 604/175 |
| 4,403,983 A | 9/1983 | Edekman et al. | |
| 4,431,426 A | 2/1984 | Groschong et al. | |
| 4,451,252 A | 5/1984 | Martin | |
| 4,493,696 A | 1/1985 | Uldall | |
| 4,543,087 A | 9/1985 | Sommercorn et al. | |
| 4,549,879 A | 10/1985 | Groshong et al. | |
| 4,559,046 A | 12/1985 | Groshong et al. | |
| 4,568,329 A | 2/1986 | Mahurkar | |
| 4,583,968 A | 4/1986 | Mahurkar | |
| 4,623,327 A | 11/1986 | Mahurkar | |
| 4,643,711 A | 2/1987 | Bates | |
| 4,682,978 A | 7/1987 | Martin | |
| 4,692,141 A | 9/1987 | Mahurkar | |
| 4,795,439 A | 1/1989 | Guest | |
| 4,808,155 A | 2/1989 | Mahurkar | |
| 4,895,561 A | 1/1990 | Mahurkar | |
| 4,935,004 A | 6/1990 | Cruz | |
| 4,985,014 A | 1/1991 | Orejola | |
| 4,995,865 A | 2/1991 | Gahara et al. | |
| 5,057,073 A | 10/1991 | Martin | |
| 5,106,368 A | 4/1992 | Uldall et al. | |
| 5,156,592 A | 10/1992 | Martin et al. | |
| 5,221,255 A | 6/1993 | Mahurkar et al. | |
| 5,221,256 A | 6/1993 | Mahurkar | |
| 5,348,536 A | * 9/1994 | Young et al. | .................. 604/43 |
| 5,378,230 A | 1/1995 | Mahurkar | |
| 5,486,159 A | 1/1996 | Mahurkar | |
| 5,643,228 A | * 7/1997 | Schucart | ...................... 604/264 |

OTHER PUBLICATIONS

"For Access Via the Internal Jugular Vein . . . the Medcomp TESEO Catheter is the Solution" (brochure), MEDCOMP, Harleysville, PA, (undated).
"Extra Flow" (brochure), Horizon Medical Products, Inc., Manchester, GA, 1997.
"Groshong CV Catheter—Acute Care" (brochure), Catheter Technology Corporation, Salt Lake City, UT, 1986–87.
"Pheres–Flow—The Apheresis–BMT Catheter Solution" (brochure), Horizon Medical Products, Inc., Manchester, GA, 1998.
"Products for Dialysis" (brochure), Cook Critical Care, Bloomington, IN, 1995.
"The Complete Source for Innovative Dialysis Access" (brochure), Bard Access Systems, Salt Lake City, UT—Vas–Cath Incorporated, Mississauga, Ontario, Canada, 1995.

* cited by examiner

Primary Examiner—Manuel Mendez
(74) Attorney, Agent, or Firm—Brinks Hofer Gilson & Lione

(57) ABSTRACT

A catheter for use in the withdrawal or delivery of a fluid to a patient. The catheter includes an elongate body having outer and inner walls and an axial passageway extending the length thereof. The body has a proximal end and a terminal end. A plurality of secondary ports are located adjacent the primary port. The secondary ports are spaced apart from the primary port and from each other. The secondary ports have a radial passageway that forms an angle greater than 20° with respect to an axis of the axial passageway.

40 Claims, 6 Drawing Sheets

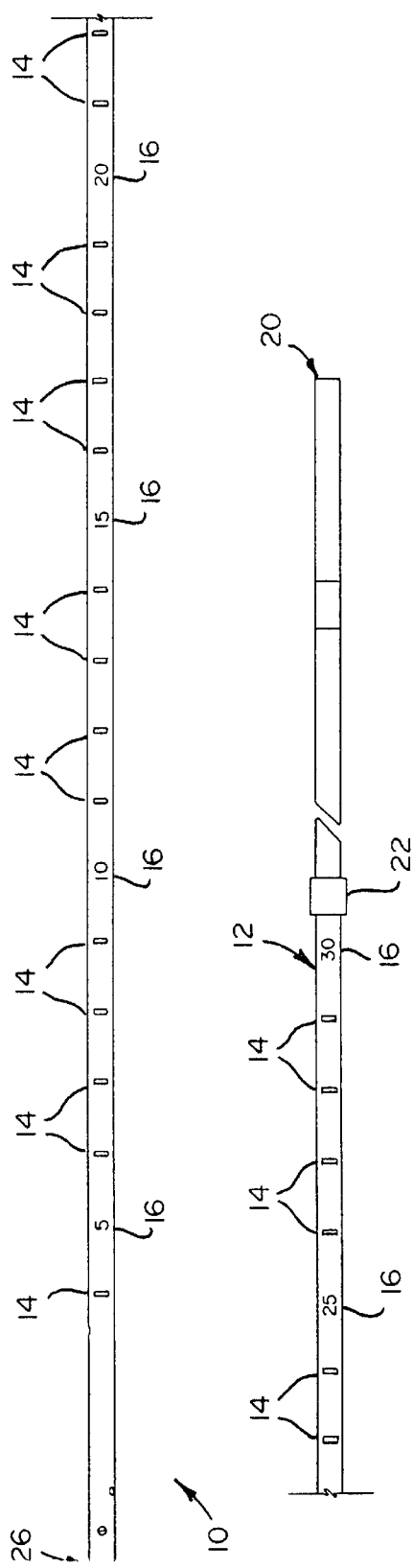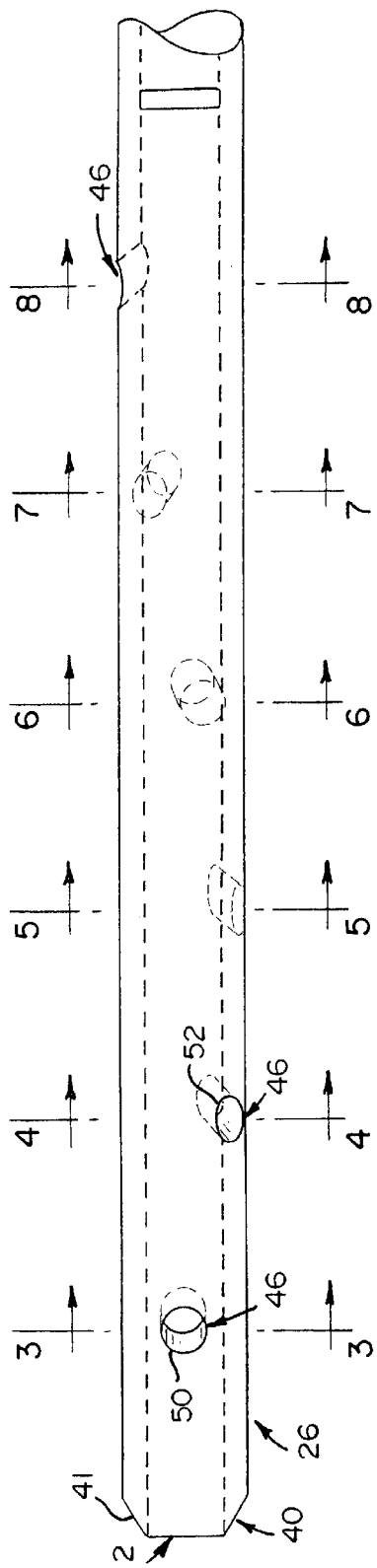

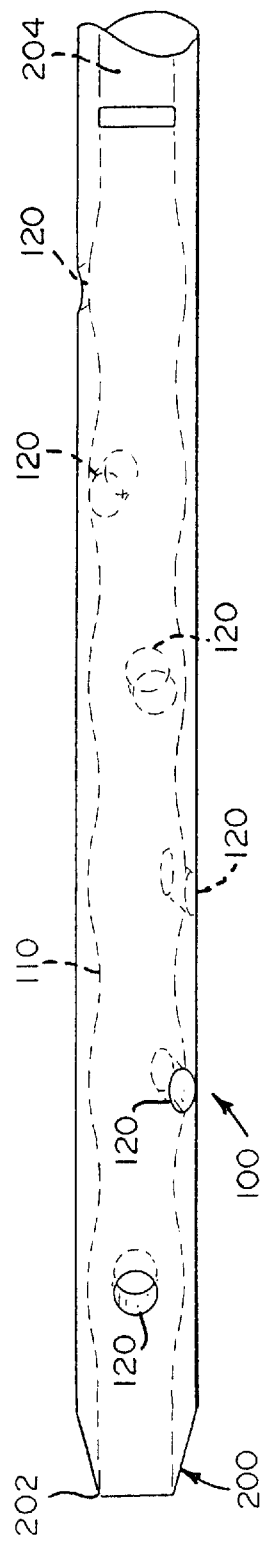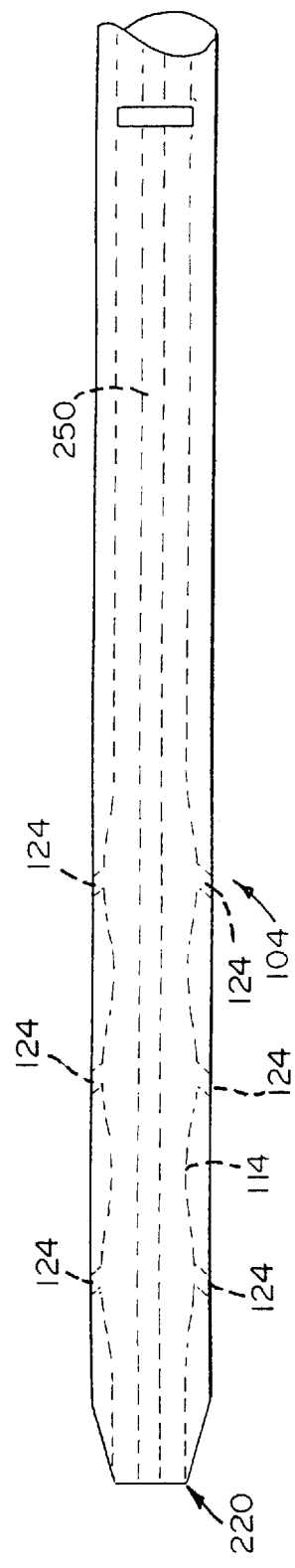

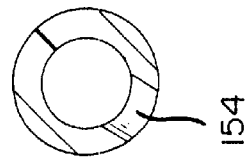
FIG. 12  FIG. 13  FIG. 14
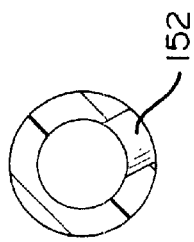
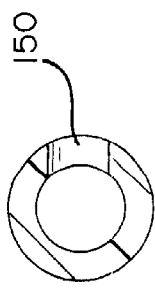
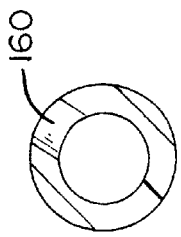
FIG. 15  FIG. 16  FIG. 17
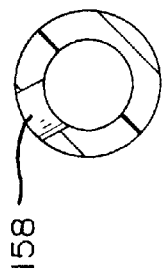
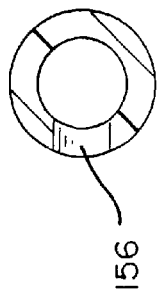

HARMONIC FLOW CATHETER

FIELD OF THE INVENTION

The present invention relates generally to the field of catheters for use in the removal and/or delivery of a fluid to a patient. More specifically, the present invention relates to a catheter having an improved fluid flow rate and reduced fluid pressure.

BACKGROUND OF THE INVENTION

Various medical procedures require the use of a catheter for the removal and/or delivery of a fluid to a patient. One example is the excorporeal treatment of blood, e.g., hemodialysis. The use of a catheter for hemodialysis requires a first lumen that accommodates blood flow from the patient (arterial lumen) in order to treat the blood and thereby remove various toxins. A second lumen is required in order to return the treated blood to the patient (venous lumen).

One previous type of catheter included an aspiration port and an infusion port opening from the end of a single catheter. However, there are several disadvantages with this design. In particular, the placement of a single aspiration and infusion port at the end of a catheter is problematic because of the risk of occlusion. Catheter ports can become partially or totally occluded by a build-up of thrombused blood, fibrin sheathing and/or drug residuals. Moreover, thrombused blood in catheter lumens or ports has been shown to be a nidus for infection. Obviously, these problems drastically reduce the effectiveness of the treatment, increase patient risk and frequently require clinical intervention with a lysing agent to restore patency.

Another problem with all types of catheters that are used to aspirate blood from a vessel is the suction pressure at the aspiration port. The suction pressure required to aspirate blood frequently causes the aspiration port to be occluded by intimal tissues within the vein resulting in tissue damage and clotting.

One attempt to resolve the problems created by occlusion and improve flow rates requires the use of additional smaller ports in the catheter prior to the terminal end. Previously, these smaller ports have extended perpendicular to the fluid flow path so as to form a 90° angle. While such smaller ports were intended to solve the problem of occlusion, they can cause other more severe problems. In particular, such previous catheters can increase the shearing of blood cells passing into and out of these smaller ports. The shearing of blood cells can result in problems such as the buildup of thrombused blood cells (clots) that can become dislodged and pass through the blood stream. Additionally, these smaller ports quickly become occluded due to the difficulty of flushing ports that are perpendicular to the fluid flow path. These occluded ports can serve as a nidus for bacterial colonization requiring antibiotic intervention and/or catheter removal and replacement.

Accordingly, there exists a need for a catheter with improved flow rates and reduced fluid pressure capable of overcoming the above-identified problems.

SUMMARY OF THE INVENTION

The present invention is directed to a catheter that improves flow rates without increasing fluid pressure, reduces turbulence around the ports, improves laminar flow around the outside of the catheter, and minimizes vessel trauma during use. A catheter embodying the present invention also reduces the possibility of occlusions and infections while minimizing the shearing effects on any fluid passing through the catheter.

The foregoing is realized in accordance with the present invention by providing an improved catheter for use in the withdrawal or delivery of a fluid to a patient. The catheter includes an elongate body having an outer and inner wall and an axial passageway extending the length thereof. The body has a proximal end, a terminal end and a primary port. A plurality of secondary ports are located adjacent the primary port. The secondary ports are spaced apart from the primary port and from each other. At least one of the secondary ports having a passageway that forms an angle greater than 20° with respect to an axis of the axial passageway.

According to another aspect of the invention, a catheter system for use in the withdrawal and delivery of a fluid to a patient is provided. The system includes a first catheter and a second catheter. The first and second catheters each have an elongate body with an axial passageway extending the length thereof. The body of each catheter has a proximal end, a terminal end and a primary port. A plurality of secondary ports are spaced apart from the primary port and from each other. The secondary ports each include a radial passageway that forms an angle greater than 20° with respect to an axis of said axial passageway.

According to another aspect of the invention, a catheter for use in at least one of the withdrawal and delivery of a fluid to a patient is provided. The catheter includes an elongate body having outer and inner walls and an axial passageway extending the length thereof. The body has a primary port, a proximal end and a terminal end. A plurality of secondary ports are spaced apart from the primary port and from each other. The axial passageway adjacent at least some of the secondary ports has a fluted shape.

According to yet another aspect of the invention, a kit for use with hemodialysis or the like is provided. The kit includes a first catheter having a first lumen for use with the aspiration of fluid from a patient. The kit also includes a second catheter having a second lumen for use with the delivery of a fluid to a patient. The lumen of the first catheter being substantially larger than the lumen of the second catheter.

The present invention, together with attendant objects and advantages, will be best understood with reference to the detailed description below in connection with the attached drawings.

BRIEF DESCRIPTION OF THE DRAWINGS

FIG. 1 is an illustration of a catheter having a chamfered tip in accordance with a first embodiment of the present invention;

FIG. 2 is an enlarged and broken away view of the terminal end of the catheter as illustrated in FIG. 1 with the inner wall and some of the secondary ports shown in dashed lines;

FIG. 9 is an illustration of a second preferred embodiment of the present invention having another chamfered tip;

FIG. 10 is an illustration of a third preferred embodiment of the present invention having a double lumen and a chamfered tip as illustrated in FIG. 9;

FIG. 12 is a cross-section taken along the lines 12—12 of FIG. 11;

FIG. 13 is a cross-section taken along the lines 13—13 of FIG. 11;

FIG. 14 is a cross-section taken along the lines 14—14 of FIG. 11;

FIG. 15 is a cross-section taken along the lines 15—15 of FIG. 11;

FIG. 16 is a cross-section taken along the lines 16—16 of FIG. 11;

FIG. 17 is a cross-section taken along the lines 17—17 of FIG. 11;

DETAILED DESCRIPTION OF THE PREFERRED EMBODIMENTS

Figure 3:
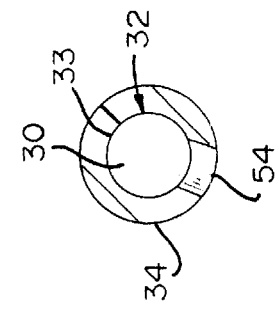
FIG. 3 is a cross-section taken along the lines 3—3 of FIG. 2.
Figure 4:
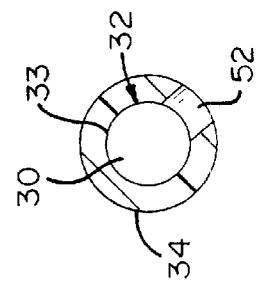
FIG. 4 is a cross-section taken along the lines 4—4 of FIG. 2.
Figure 5:
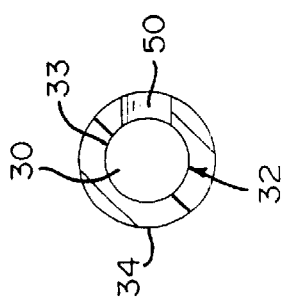
FIG. 5 is a cross-section taken along the lines 5—5 of FIG. 2.
Figure 8:
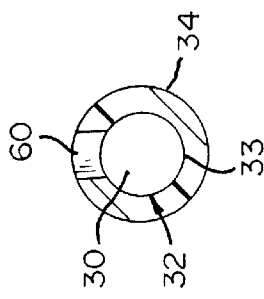
FIG. 8 is a cross-section taken along the lines 8—8 of FIG. 2.
Figure 7:
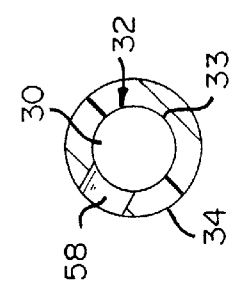
FIG. 7 is a cross-section taken along the lines 7—7 of FIG. 2.
Figure 6:
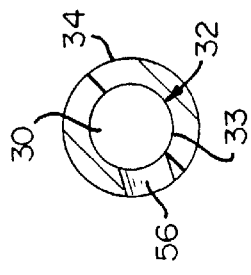
FIG. 6 is a cross-section taken along the lines 6—6 of FIG. 2.

The preferred embodiments are described herein in the context of catheters, generally. The principles of the invention apply equally well to all types of catheters, including Foley catheters, urethral catheters, central venous catheters and ports, plural cavity effusion catheters, peripherally inserted central catheters, mid-lines and other catheters useful in a wide range of diverse applications such as hemodialysis, vascular access and many others.

Referring now to the drawings, and particularly to FIGS. 1–8, a catheter illustrating a first embodiment of the present invention is seen generally at 10. The catheter 10 includes an elongate and substantially cylindrical tube body 12, although other shapes such as oval, elliptical and oblong may be implemented. The tube body 12 is preferably fabricated from a resilient, biocompatible and thermoset material such as silicone. Other biocompatible materials such as polyurethane may also be used. Silicone is the preferred material for use with blood and blood products such as encountered during hemodialysis or any other type of long-term venous access. The tube body 12 has a durometer reading which is preferably within the range of 60 D to 80 D. The dimensions of the tube body 12 depend upon the size of the catheter 10 in use. The present invention is useful with a wide range of French sizes, although a 10 Fr tube body 12 is illustrated.

The tube body 12 is formed from a radiopaque material and includes silicone ink stripes 14 to facilitate location of the catheter 10 within the patient by use of a fluoroscope or X-ray. The stripes 14 are uniformly placed along the entire length of the tube body 12. A printed indicia, such as the numbers 16 are also useful during the insertion of the catheter 10 into a patient.

The tube body 12 includes a proximal end 20 which may be connected to various medical devices required for the withdrawal or delivery of a fluid. Adjacent the proximal end 20 a dacron cuff 22 is located. The cuff 22 is implanted beneath the epidermis in order to anchor the catheter and to impede the migration of bacteria into the patient. The body 12 also includes a distal or terminal end 26. The terminal end 26 is best seen in FIG. 2.

With reference to FIGS. 3–8, the tube body 12 includes an axial passageway 30 defined by wall 32. The wall 32 has an inner surface 33 and an outer surface 34. The inner surface 33 and the outer surface 34 define the thickness of the wall 32. Preferably, the axial passageway 30 has a diameter of 0.086" and the wall 32 has a thickness of 0.05".

The terminal end 26 of the catheter 10 includes a tip 40. As shown in FIG. 2, the tip 40 has a first-conical end surface 41 which forms an angle of approximately 60° with a plume extending perpendicular to the tube catheter 10. Additional preferred embodiments are illustrated in FIGS. 9 and 10 where the tips 200 and 220 have an end surface which forms an angle of approximately 75°. But, as those of skill in the art will recognize, the tips 40, 200 and 220 may be formed having an angle substantially within the range of 20°–80°. The tips 40, 200 and 220 are designed to create a laminar flow around the catheter to minimize fluid turbulence, reduce the buildup of thrombused blood and/or drug residuals, and increase patency. The tips 40, 200 and 220 also reduce catheter movement within the vessel, i.e., whipping, and improve flow rates without increasing the size of the catheter or increasing fluid pressure.

A primary port 42 is also located within the terminal end 26. The primary port 42 has a circular opening with a diameter of 0.086". A plurality of secondary ports 46 are spaced at intervals from the primary port 42. In the preferred embodiment, six secondary ports 46 are located adjacent the terminal end 26. However, it should be recognized that as few as one port and more than six ports may be implemented with the present invention. The secondary ports 46 are spaced apart longitudinally from each other approximately 0.228" in the preferred embodiment. The secondary ports 46 are preferably circular in shape and have a diameter of 0.05". Alternatively, the secondary ports 46 can be oval, oblong, elliptical or the like and have diameters of varying size described with respect to the embodiments of FIGS. 11–17.

In the preferred embodiment, the secondary ports 46 form a 45° angle with respect to an axis of the axial passageway 30. Yet, it should be recognized that the secondary ports 46 could form other angles including those substantially within the range of 20°–70° and, more preferably, 40–50°.

With one exception in the preferred embodiment, the secondary ports 46 are angularly spaced from one another about the axis of the catheter 10 by an angle of approximately 54° as illustrated in FIGS. 3–7. The first port 50, and the second port 52 and so on through the sixth port 60, are angularly spaced apart from each other approximately 54°. However, the first port 50 and the sixth port 60 are angularly spaced from each other by an angle of approximately 90° as illustrated in FIGS. 3 and 9. This arrangement of the secondary ports 46 creates a spirodactic pattern. The spirodactic pattern is important because it provides for the preferred number of ports while not substantially compromising the rigidity of the catheter 10 near its terminal end 26. Alternatively, the ports can be separated by angles within the range of 30–60°, e.g., 30°, 40° or 60°. Of course, the first port and sixth port may be separated by an angle different than that of the other ports in the case of a 30° or 40° separation pattern. In the case of a 300 separation pattern, all of the ports will be located on one side of the catheter.

Figure 18:
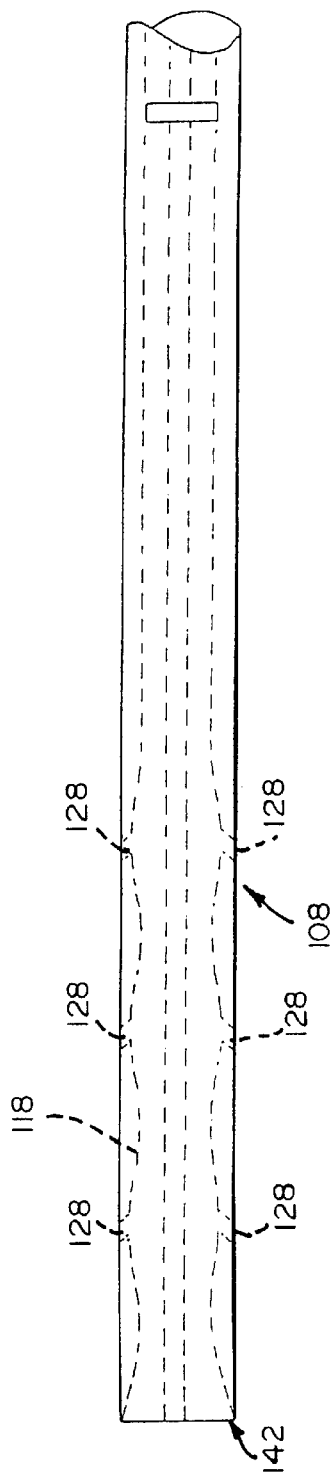
FIG. 18 is an illustration of a fifth preferred embodiment of the present invention having a funnel-shaped tip and a double lumen.

In hemodialysis, two catheters embodying features of the present invention are used. One catheter is useful for the removal of blood (arterial catheter) and the other catheter is useful for the delivery of treated blood (venous catheter). These catheters are positioned within the superior vena cava such that the distal ends are displaced approximately 3 cm to avoid recirculation. Two catheters (such as those illustrated in FIGS. 1, 9 or 11) may be implemented for this particular purpose. Alternatively, a double lumen catheter as illustrated in FIGS. 10 and 18 may be used.

FIGS. 9–11 and 18 illustrate further preferred embodiments of the present invention that are constructed in generally the same manner as the embodiments of FIGS. 1 and 9, with the exception that the inner surfaces of their walls are "fluted" or undulate along at least a portion of the axial passageway in the terminal end of the catheter. The catheters 100, 104, 106 and 108 have fluted or undulating inner wall surfaces 110, 114, 116 and 118 adjacent the secondary ports 120, 124, 126 and 128. The fluted inner wall surfaces enhance the harmonic fluid flow at the secondary ports 120, 124, 126, and 128. The cross-sectional area of the passageway through the catheters 100, 104, 106, and 108 is increased adjacent the secondary ports 120, 124, 126 and 128. As a result, the volume of fluid through the passageway is increased adjacent the secondary ports 120, 124, 126 and 128. This reduces fluid pressure and shearing forces on the fluid passing out of, or into, the secondary ports 120, 124, 126 and 128.

In addition, the undulating inner wall surfaces 110, 114, 116, and 118 cause the secondary ports 120, 124, 126 and 128 to have a reduced length. The reduced length of the secondary ports 120,124,126 and 128 reduces the surface area available for the buildup of thrombused blood and/or drug residuals. The double-lumen catheters 104 and 108 operate in essentially the same manner as do the catheters 100 and 106.

In a preferred embodiment, the tube walls have a thickness that varies between 0.038" and 0.026" in a 10 F single lumen catheter. However, depending upon the size and type (single or multi-lumen) of catheter, the tube walls could have a thickness of between 0.010" and 0.45". The catheters 106 and 108 operate in essentially the same manner as the catheters 110 and 114 except that funnel-shaped tips 140 and 142 are implemented to improve aspiration and to initialize harmonic flow within the lumen.

Figure 11:
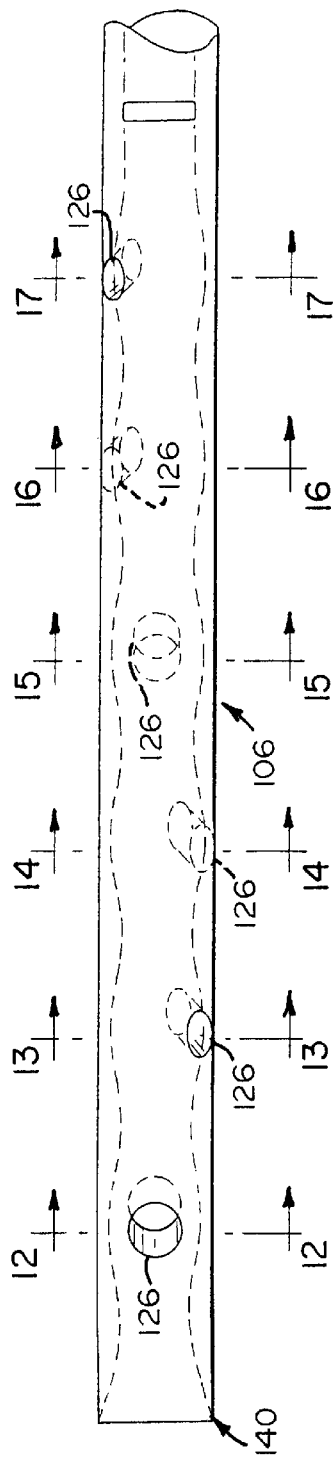
FIG. 11 is an illustration of a fourth preferred embodiment of the present invention having a funnel-shaped tip.

The embodiments of FIGS. 11 and 18 include secondary ports having varying diameters. With respect to the embodiment of FIG. 11, FIGS. 12–17 illustrate the varying diameter of the secondary ports 126 with each port being equally angularly spaced apart. The first port 150 (FIG. 12) has a diameter is 0.624" in the preferred embodiment. The second port 152 (FIG. 13) has a diameter of 0.60" and third port 154 (FIG. 14) has a diameter of 0.0576". The fourth port 156 (FIG. 15) has a diameter of 0.55" and the fifth port 158 (FIG. 16) has a diameter of 0.526". The sixth or last port 160, as illustrated in FIG. 17, has a diameter of 0.50".

As illustrated in the Figures, the first port 150 has a larger diameter than the last port 160 with the intervening ports having increasing smaller diameters therebetween. This results in a gradual increase in the volume of fluid flowing into the catheter. By gradually increasing the volume and velocity of the fluid into the catheter coupled with the harmonic flow within the fluted chambers, the shearing forces on the fluid are dramatically decreased. Additionally, by gradually increasing the volume of the fluid entering the catheter, the pressure on the fluid is reduced, permitting increased flow rates, This principle works equally well on catheters for use with aspiration (arterial) and infusion (venous).

The external surface of the chamfered tip 200 illustrated in FIG. 9 is preferably formed with an included angle of approximately 75° relative to a vertical plane extending transversely through the end 202 of the tip 200. The tip 200 may, however, have an angle of between 20°–80°. The chamfered tip 200 creates a reduced wall thickness which is radially expandable when pressure builds up in the axial passageway 204 of the catheter 100. In particular, by applying pressure through the introduction of normal saline solution to the axial passageway 204 of the catheter 100, the chamfered tip 200 will be expanded when an occlusion is located therein. By expanding the chamfered tip 200, the occlusion will be released. As a result, the occluded tip can frequently be cleared without the use of a costly lysing agent. The embodiments of FIGS. 10, 11 and 18 operate in essentially the same way, except that the embodiments of FIGS. 10 and 18 include a double lumen and the embodiments of FIGS. 11 and 18 include a funnel-shaped tip.

The catheters 10, 100, 104, 106 and 108 may be molded around a fluted mandrel with removable stems to form the angled side ports. Alternatively, approximately the last two inches of the terminal end of the catheter could be injection molded and then bonded to the remaining portion of the catheter forming the terminal end thereof. This approach would be particularly useful with a dual or multi-lumen catheter.

Figure 19:
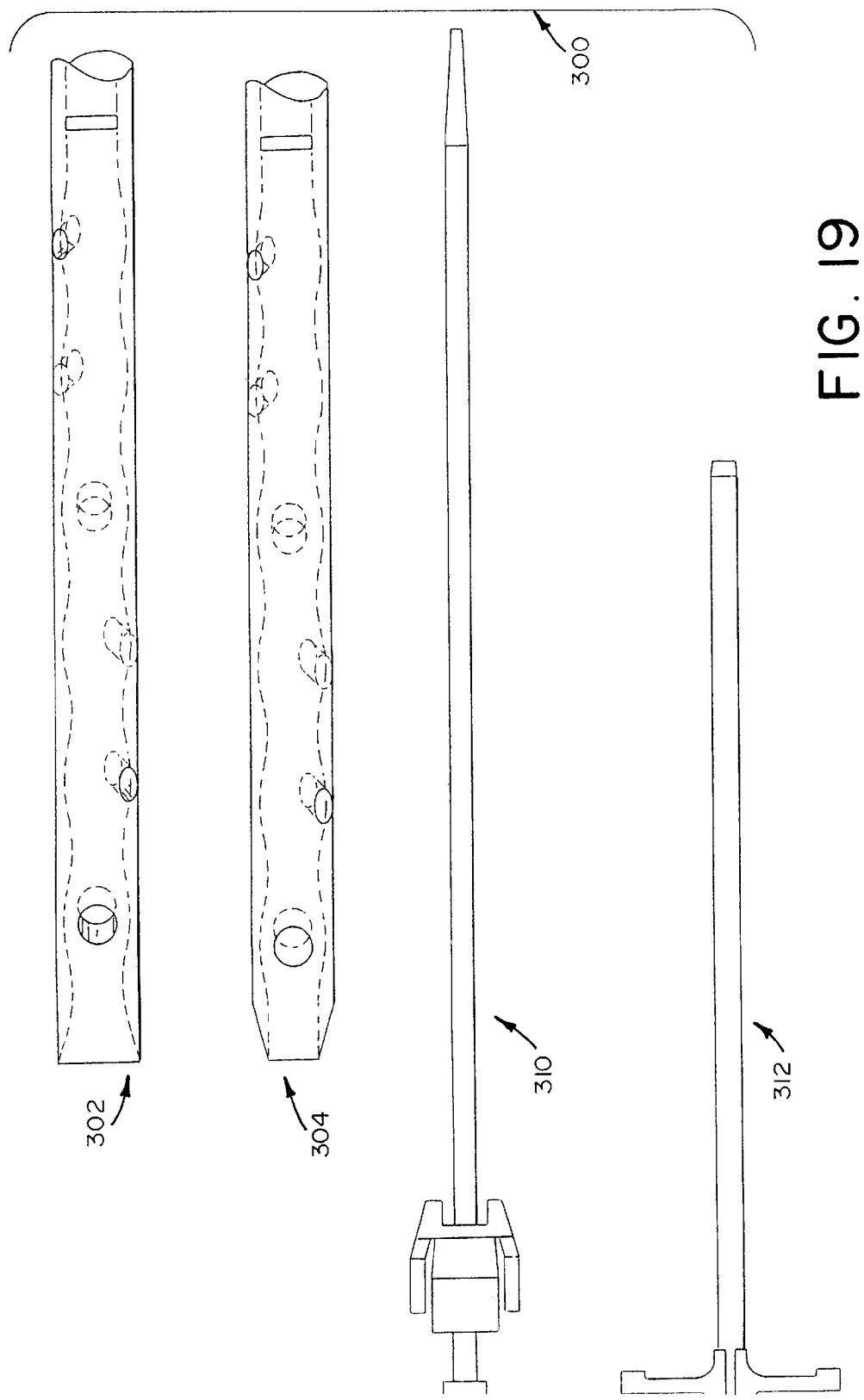
FIG. 19 is an illustration of a kit in accordance with a sixth preferred embodiment of the present invention.

FIG. 19 illustrates a hemodialysis kit 300 constructed in accordance with another preferred embodiment of the invention. The kit 300 includes two catheters 302 and 304 (substantially as described with respect to FIGS. 9 and 11). However, it should be recognized that the two catheters of the present invention can include any two single lumen catheters as described herein or otherwise known to those of ordinary skill in the art. The catheter 302 is a 10.6 F for use the removal or aspiration of a fluid. The catheter 304 is a 10.0 F catheter for use with the delivery or infusion of a fluid. Accordingly, a larger volume of a fluid may be drawn into the catheter 302 without increasing the resulting pressure. In blood, for example, this produces the advantage of less shearing force applied to the blood cells while increasing the volume of fluid passing therethrough. A conventional 11 F dialator 310 and peel-away sheath 312, as available from DAIG, Inc. of Minnetonka, Minn., are used to insert both catheters 302 and 304. Because the catheter 302 is only 10.6 F, the same 11 F dialator 310 and peel-away sheath 312 can be used with both catheters 302 and 304.

The embodiments described above and shown herein are illustrative and not restrictive. The scope of the invention is indicated by the claims rather than by the foregoing description and attached drawings. The invention may be embodied in other specific forms without departing from the spirit of the invention. For example, the size, number and shape of the secondary ports may be designed in a manner other than as specifically illustrated in the figures, Also, the present invention may be used with catheters having a wide variety of French sizes and uses. Accordingly, these and any other changes which come within the scope of the claims are intended to be embraced herein.

I claim:

1. A catheter for use in the withdrawal and/or delivery of a fluid to a patient, comprising:
   a) an elongate tube body;
   b) the tube body including a wall having inner and outer surfaces defining the thickness of the wall along the length of the body, the inner surface forming an axial passageway extending through the body in between a proximal end and a terminal end of the body;

c) the tube body having a primary port for at least one of the withdrawal or delivery of a fluid through the passageway; and d) the tube Lady having a plurality of secondary ports extending through the wall at locations in the body spaced from the primary port and from each other, the ports having a diameter of substantially 0.50" or larger;

e) the secondary ports having a passageway that forms an angle greater than 20° and less than 70° with respect to an axis of the axial passageway.

2. The catheter of claim 1 wherein at least one of the secondary ports form an angle within the range of 20°–70° with respect to the axis of the axial passageway.

3. The catheter of claim 2 wherein at least one of the secondary ports forms an angle substantially equal to 45° with respect to the axis.

4. The catheter of claim 3 wherein there are six or fewer of the secondary ports.

5. The catheter of claim 4 wherein the secondary ports are substantially equally spaced apart along a length of the tube body.

6. The catheter of claim 5 wherein some of the secondary ports have a diameter greater than half of a diameter of the primary port.

7. The catheter of claim 6 wherein the secondary ports form a spirodactic pattern.

8. The catheter of claim 7 wherein the secondary ports include a first port and an end port, the first port being spaced adjacent to the primary port and having a diameter larger than a diameter of the end port.

9. The catheter of claim 2 wherein the catheter includes a tip having a funnel shape.

10. A catheter for use with at least one of the withdrawal and delivery of a fluid to a patient, comprising:

a) an elongate tube body having a primary port, the tube body having outer and inner surfaces, the inner surface defining an axial passageway extending a length thereof, and b) a plurality of secondary ports in the body spaced apart from the primary port and from each other, at least some of the secondary ports having a harmonic fluid flow path.

11. The catheter of claim 10 wherein at least some of the secondary ports form an angle within the range of 20°–70° with respect to an axis of the axial passageway of the tube body.

12. The catheter of claim 11 wherein at least some of the secondary ports have different diameters.

13. The catheter of claim 12 wherein the secondary ports comprise six or fewer ports.

14. The catheter of claim 13 wherein the secondary ports are substantially equally spaced apart along said tube body.

15. The catheter of claim 14 wherein the catheter includes a laminar flow chamfer tip.

16. The catheter of claim 10 wherein the catheter includes a tip having a funnel shape.

17. A catheter system for use with at least one of the withdrawal and delivery of a fluid to a patient, comprising:

a) a first catheter and a second catheter;

b) the first and second catheters each having an elongate tube body with an axial passageway extending substantially the length thereof, the body of each catheter having a proximal end and a terminal end, and c) a plurality of secondary ports in the body spaced apart from the primary port and from each other, the secondary ports each including a radial passageway that forms an angle greater than 20° and less than 70° with respect to an axis of the axial passageway, at least two of the ports having different diameters.

18. The catheter system of claim 17 wherein the secondary ports form an angle within the range of 20°–70°.

19. The catheter system of claim 18 wherein the secondary ports comprise six or fewer ports.

20. The catheter system of claim 19 wherein the secondary ports are substantially equally spaced apart along a length of the catheter.

21. The catheter system of claim 20 wherein the terminal end has a funnel-shaped tip.

22. The catheter system of claim 20 wherein the terminal end has a laminar flow chamfer tip.

23. The catheter system of claim 18 wherein the secondary ports form an angle substantially equal to 45°.

24. The catheter system of claim 23 wherein the secondary ports include a first hole and a last hole and a plurality of intermediate holes, the first hole and the last hole being spaced angularly apart different than the intermediate holes.

25. The catheter system of claim 17 wherein the first hole and the last hole have different diameters.

26. A catheter for use in the withdrawal and/or delivery of a fluid to a patient, said catheter comprising:

an elongate body having outer and inner walls and an axial passageway extending the length thereof, the cylindrical body having a proximal end and a terminal end, the terminal end having a laminar flow tip and a primary port for the withdrawal or delivery of a fluid to a patient, and a plurality of secondary ports spaced apart from the primary port and from each other, at least some of the secondary ports having a passageway that forms an angle greater than 20° and less than 70° with respect to an axis of the axial passageway, substantially the entire passageway being formed at an angle greater than 20° with respect to the axis of the axial passageway, the ports having a diameter of substantially 0.50" or larger.

27. The catheter of claim 26 wherein the tip has an angle within the range of 20°–80°.

28. The catheter of claim 27 wherein the tip has an angle of substantially 75°.

29. A catheter for use in at least one of the withdrawal and delivery of a fluid to a patient, said catheter comprising:

an elongate body having outer and inner walls and an axial passageway extending the length thereof, the body having a primary port and a proximal end and a terminal end, and a plurality of secondary ports spaced apart from the primary port and from each other, the axial passageway adjacent at least some of the secondary ports having a fluted shape.

30. The catheter of claim 29 wherein the axial passageway has a larger cross-sectional area adjacent the secondary ports.

31. The catheter of claim 30 wherein the inner walls include at least a portion that varies substantially continuously adjacent the secondary ports.

32. The catheter of claim 31 wherein the inner walls include at least a portion having a generally curved shape adjacent the secondary ports.

33. The catheter of claim 32 wherein the secondary ports are substantially equally spaced apart along a length of the catheter.

34. The catheter of claim 33 wherein the secondary ports form an angle within the range of 20°–70° with respect to an axis of the axial passageway.

35. A catheter for use in delivery of a fluid to a patient or withdrawal of a fluid from a patient, comprising:

a) an elongate tube body;
b) said tube body including a wall having inner and outer surfaces defining the thickness of the wall along the length of the body, said inner surface forming a passageway extending axially through the body in between a proximal end and a terminal end of the body;
c) said tube body having a primary port in its terminal end for delivery or withdrawal of a fluid through the passageway; and
d) said tube body having a plurality of secondary ports extending through said wall at locations in said body spaced from said primary port and from each other; at least two of the ports having distinct diameters, and the ports having a diameter of substantially 0.50" or larger with at least some of the secondary ports having a passageway that forms an angle greater than 20° and less than 70° with respect to an axis of the axial passageway.

36. The catheter of claim 35 wherein all the secondary ports have distinct diameters.

37. The catheter of claim 36 wherein the secondary port closest to the terminal end tip has the largest diameter.

38. The catheter of claim 37 wherein the secondary port closest to the proximal end has the smallest diameter.

39. The catheter of claim 38 wherein the secondary ports have a progressively smaller diameter proceeding from the secondary port closest to the terminal end to the secondary port closest to the proximal end.

40. The catheter of claim 39 wherein the secondary ports are substantially equally spaced apart along a length of the catheter.

* * * * *

UNITED STATES PATENT AND TRADEMARK OFFICE
CERTIFICATE OF CORRECTION

PATENT NO. : 6,533,763 B1
DATED : March 18, 2003
INVENTOR(S) : James A. Schneiter It is certified that error appears in the above-identified patent and that said Letters Patent is hereby corrected as shown below:

Column 3,
Line 37, before "cavity" delete "plural" and substitute -- pleural -- in its place.

Column 4,
Line 11, before "thickness of" insert -- total --.
Line 46, delete "40-50º." and substitute -- 40º-50º. -- in its place.
Line 61, delete "30-60º," and substitute -- 30º-60º, -- in its place.
Line 64, delete "300" and substitute -- 30º -- in its place.

Column 5,
Line 30, delete "120,124,126" and substitute -- 120, 124, 126 -- in its place.
Line 39, delete "0.45" and substitute -- 0.045 -- in its place.
Line 49, delete "0.624"" and substitute -- 0.0624" -- in its place.
Line 50, delete "0.60"" and substitute -- 0.060" -- in its place.
Line 52, delete "0.55"" and substitute -- 0.055" -- in its place.
Line 53, delete "0.526"." and substitute -- 0.0526". -- in its place.
Line 54, delete "0.50"." and substitute -- 0.050". -- in its place.
Line 65, delete "rates," and substitute -- rates. -- in its place.

Column 6,
Line 54, delete "figures," and substitute -- figures. -- in its place.

Column 7,
Line 4, delete "Lady" and substitute -- body -- in its place.
Line 8, delete "0.50"" and substitute -- .050" -- in its place.
Lines 33, 44, 48, 50, 52, 54, and 56, before "catheter" insert -- pleural cavity effusion --.
Lines 40-43, delete "at least some of the secondary ports having a harmonic fluid flow path." and substitute -- the ports having a diameter of substantially .050" or larger and the secondary ports having a passageway that forms an angle greater than 20º and less than 70º with respect to an axis of the axial passageway. --.

UNITED STATES PATENT AND TRADEMARK OFFICE
CERTIFICATE OF CORRECTION

PATENT NO. : 6,533,763 B1
DATED : March 18, 2003
INVENTOR(S) : James A. Schneiter It is certified that error appears in the above-identified patent and that said Letters Patent is hereby corrected as shown below:

<u>Column 8,</u>
Line 37, delete "0.50"" and substitute -- .050" -- in its place.

<u>Column 9,</u>
Line 13, delete "0.50"" and substitute -- .050" -- in its place.

Signed and Sealed this

Ninth Day of March, 2004

JON W. DUDAS
*Acting Director of the United States Patent and Trademark Office*